United States Patent [19]
Corbin et al.

[11] Patent Number: 5,648,569
[45] Date of Patent: Jul. 15, 1997

[54] PURIFACTION OF PENTAFLUOROETHANES

[75] Inventors: David Richard Corbin, West Chester, Pa.; Dallas Wesley Reutter, Wilmington, Del.

[73] Assignee: E. I. Du Pont de Nemours and Company, Wilmington, Del.

[21] Appl. No.: 688,451

[22] Filed: Jul. 30, 1996

[51] Int. Cl.$^6$ ............................................. C07C 17/38
[52] U.S. Cl. ............................................. 570/179
[58] Field of Search ............................................. 570/179

[56] References Cited

U.S. PATENT DOCUMENTS

| | | | |
|---|---|---|---|
| 4,906,796 | 3/1990 | Yates | 570/179 |
| 4,950,816 | 8/1990 | Tung et al. | 570/179 |
| 5,087,329 | 2/1992 | Felix | 203/67 |
| 5,210,342 | 5/1993 | Moore | 570/179 |

FOREIGN PATENT DOCUMENTS

| | | |
|---|---|---|
| 3-72437 | 3/1991 | Japan . |
| 3-99026 | 4/1991 | Japan . |

OTHER PUBLICATIONS

T.W. Ebbesen & P.M. Ajayan, "Large–scale synthesis of carbon nanotubes", *Letters to Nature*, 358, pp. 220–222, 16 Jul. 1992.

Szostak, R., *Molecular Sieves: Principles of Synthesis and Identification*, Van Nostrand Reinhold, p. 2 (1989).

*Primary Examiner*—Alan Siegel

[57] ABSTRACT

Mixtures of $CClF_2CF_3$ (CFC-115) and $CHF_2CF_3$ (HFC-125) can be substantially separated by using carbon nanotubes as a sorbent for $CClF_2CF_3$. A process is described for treating a starting mixture of $CHF_2CF_3$ and $CClF_2CF_3$ to provide a product wherein the mole ratio of $CHF_2CF_3$ to $CClF_2CF_3$ is increased relative to the mole ratio of $CHF_2CF_3$ to $CClF_2CF_3$ in the starting mixture; and another process (involving desorbing sorbed $CClF_2CF_3$) is disclosed for treating a starting mixture of $CClF_2CF_3$ and $CHF_2CF_3$ to provide a product mixture wherein the mole ratio of $CClF_2CF_3$ to $CHF_2CF_3$ is increased relative to the mole ratio of $CClF_2CF_3$ to $CHF_2CF_3$ in the starting mixture. The process for producing a $CHF_2CF_3$-enriched product and the process for producing a $CClF_2CF_3$-enriched product may be integrated into an overall process (e.g., a thermal swing cycle process) where both of said products are provided. Production of high purity HFC-125 is disclosed.

8 Claims, No Drawings

PURIFACTION OF PENTAFLUOROETHANES

This application claims the priority benefit of U.S. Provisional application 60/001,799 filed Aug. 2, 1995 now abandoned.

FIELD OF THE INVENTION

This invention relates 16 the separation of mixtures of halogenated hydrocarbons containing fluorine, and more particularly to the separation of mixtures containing chloropentafluoroethane (i.e., $CClF_2CF_3$ or CFC-115) and pentafluoroethane (i.e., $CHF_2CF_3$ or HFC-125).

BACKGROUND

Products containing pentafluoroethane (i.e., pentafluoroethane products) are produced in various degrees of purity. HFC-125 is commonly prepared by chlorofluorinating perchloroethylene to produce a mixture including 1,1,2-trichlorotrifluoroethane (CFC-113), 1,2-dichlorotetrafluoroethane (CFC-114) and 2,2-dichloro-1,1,1-trifluoroethane (HCFC-123); removing 1,1,2-trichlorotrifluoroethane; and fluorinating the remaining mixture by various processes to produce a product containing pentafluoroethane (HFC-125) and chloropentafluoroethane (CFC-115) as well as smaller amounts of other fluorinated compounds (e.g., hexafluoroethane, FC-116). Various other methods for making pentafluoroethane also result in mixtures with significant amounts of chloropentafluoroethane. For example, HFC-125 can be produced by the hydrogenolysis of CFC-115 (see, e.g., Japanese Kokai No. 03/099026).

HFC-125 is a valuable non-chlorine containing fluorocarbon that is especially useful as a refrigerant, blowing agent, propellant, fire extinguishing agent or sterilant carrier gas. It has been found that for many of these applications, the presence of CFC-115 can significantly alter the physical properties of HFC-125. Furthermore, CFC-115 as a chlorine-containing halocarbon can reportedly have a deleterious effect on the stratospheric ozone layer. As a result, there have been continually increasing market and process demands for high purity $CHF_2CF_3$. Consequently, identification of methods of separation represents a significant aspect of preparing HFC-125 for specific applications.

Purification of halogenated hydrocarbon products has been the subject of considerable research. Of particular interest are the challenges presented in separating a halogenated hydrocarbon from materials such as impurities in the starting materials used to produce the halogenated hydrocarbon, excess reactants, and reaction co-products and by-products which are difficult to remove by standard separation methods such as distillation. Mixtures of pentafluoroethane and chloropentafluoroethane can be nearly azeotropic. The boiling points of the halogenated hydrocarbons are very close (−48.5° C. for pentafluoroethane and −38.7° C. for chloropentafluoroethane). Furthermore, their relative volatility is below 1.1 at concentrations of pentafluoroethane greater than 87.5 mole percent and below 1.01 at concentrations of pentafluoroethane greater than 95 mole percent. The boiling points and relative volatilities indicate that it is extremely impractical to recover substantially pure pentafluoroethane from such mixtures by simple distillation.

Both carbon based and zeolite based sorbents have been proposed for various separations. The effectiveness of separation with either sorbent varies with the chemical components and the sorbents involved. The successful design of sorbent based systems is considered highly dependent upon experimental determination of whether the relative sorbencies of the particular compounds are suitable for such systems.

SUMMARY OF THE INVENTION

In accordance with the present invention, mixtures of $CClF_2CF_3$ (CFC-115) and $CHF_2CF_3$ (HFC-125) can be substantially separated by using carbon nanotubes as a sorbent for $CClF_2CF_3$. The present invention provides a process for treating a starting mixture of $CHF_2CF_3$ and $CClF_2CF_3$ to provide a product wherein the mole ratio of $CHF_2CF_3$ to $CClF_2CF_3$ is increased relative to the mole ratio of $CHF_2CF_3$ to $CClF_2CF_3$ in the starting mixture. This process comprises contacting said starting mixture with said sorbent at a temperature within the range of about −20° C. to 75° C. and a pressure within the range of about 10 kPa to 3000 kPa and for a period of time sufficient to remove a substantial amount of the $CClF_2CF_3$. As a result, the mole ratio of $CHF_2CF_3$ to $CClF_2CF_3$ increases (preferably such that the relative amount of CFC-115 in the product is no more than 50% of the relative amount of CFC-115 in the starting mixture); and a product wherein the mole ratio of $CHF_2CF_3$ relative to $CClF_2CF_3$ is increased, may thus be recovered. This aspect of the present invention provides a method for providing a high purity HFC-125.

This invention also provides a process for treating a starting mixture of $CClF_2CF_3$ and $CHF_2CF_3$ to provide a product wherein the mole ratio of $CClF_2CF_3$ to $CHF_2CF_3$ is increased relative to the mole ratio of $CClF_2CF_3$ to $CHF_2CF_3$ in the starting mixture. This process comprises contacting the starting mixture with said sorbent as described above to remove a substantial amount of the $CClF_2CF_3$, and desorbing sorbed $CClF_2CF_3$ to provide a product which is enriched therewith. The process for producing a $CHF_2CF_3$-enriched product and the process for producing a $CClF_2CF_3$-enriched product may be integrated into an overall process (e.g., a thermal swing cycle process) whereby both of said products are provided.

DETAILS OF THE INVENTION

The present invention provides for the separation of CFC-115 from HFC-125. A process is provided in accordance with this invention for providing a high purity HFC-125 product which comprises the step of contacting mixtures of $CClF_2CF_3$ (CFC-115) and $CHF_2CF_3$ (HFC-125) with a sorbent consisting of carbon nanotubes (i.e., buckytubes) at a temperature and pressure suitable for sorption, for a period of time sufficient to remove a substantial mount of CFC-115. Prior to separation (i.e., contact with the carbon nanotubes), the HFC-125/CFC-115 mix preferably has a mole ratio of $CHF_2CF_3$ to $CClF_2CF_3$ of at least about 9:1; more preferably a mole ratio of at least about 19:1; and most preferably a mole ratio of at least about 99:1.

A mixture of HFC-125 and CFC-115 may result, for example, from the hydrogenolysis of CFC-115 in the presence of catalysts containing platinum-group metals at an elevated temperature (e.g., 320° C.). Unreacted starting material may be recycled and reacted further to produce additional HFC-125. Additional impurities may also be present in such products. Distillation is typically used in order to remove impurities such as hydrogen fluoride, hydrogen chloride, and tars to produce a product which has at least about 90 mole percent HFC-125. Further purification according to this invention may then be advantageously employed. This invention can thus be adapted to provide an improvement to a process for producing pure quantities of HFC-125.

The carbon nanotubes can be prepared by the procedure of Ajayan et al. in "Large-scale synthesis of carbon nanotubes", Nature, 358 (1992) 220–222, incorporated by reference herein.

Suitable temperature ranges for sorption using carbon nanotubes range from about −20° C. to about 75° C. Suitable pressures for sorption range from about 10 kPa to about 3000 kPa.

Contact with sorbent should be sufficient to achieve the desired degree of HFC-125 enrichment. Preferably, the contact is sufficient to provide a product wherein the mole ratio of CFC-115 to HFC-125 therein is no more than 50% of the mole ratio amount of CFC-115 to HFC-125 in the starting mixture. A particularly advantageous embodiment of this invention involves providing sufficient sorbent contact to produce $CHF_2CF_3$ of at least about 99.9 mole percent purity. This is facilitated by using an initial mixture consisting essentially of CFC-115 and HFC-125.

This invention can be practiced with the sorbent contained in a stationary packed bed through which the process stream whose components need separation is passed. Alternatively, it can be practiced with the sorbent applied as a countercurrent moving bed or as a fluidized bed where the sorbent itself is moving. It can be applied with the sorbent contained as a stationary packed bed but the process configured as a simulated moving bed, where the point of introduction to the bed of the process stream requiring separation is changed, such as may be effected using appropriate switching valves.

The production of purified $CHF_2CF_3$ may be accompanied by the production of other products which are enriched with regard to the concentration of one or more other components of the initial mixture. Products enriched with respect to some compounds (e.g., CFC-115) are commonly obtained by desorption following $CHF_2CF_3$ purification. Desorption of components held by the sorbent may be effected with the sorbent left in place, or the sorbent may be removed and the desorption effected remotely from where the sorption step occurred. These desorbed components may exit the sorbent section in a direction either co-current (in the same direction as the original stream requiring separation was fed) or countercurrent (in the opposite direction of the original stream requiring separation). Such desorption may be effected with or without the use of a supplemental purge liquid or gas flow, this purge material being any one of the component materials, or some appropriate alternative material, similarly fed either co-currently or countercurrently.

In general, desorption can be effected by changing any thermodynamic variable which is effective in removing the sorbed components from the sorbent. For example, sorption and desorption may be effected using a thermal swing cycle, (e.g., where after a period of sorption, the sorbent is heated externally through the wall of the vessel containing it, and/or by the feeding of a hot liquid or gas into the sorbent, the hot gas being either one of the component materials or alternative materials). Alternatively, the trace components can be removed by using a pressure swing cycle or vacuum swing cycle (e.g., where after a period of sorption, the pressure is sufficiently reduced, in some embodiments to a vacuum, such that sorbed components are desorbed). Alternatively, the sorbed components can be removed by use of some type of stripping gas or liquid, fed co-currently or countercurrently to the original process feed material. The stripping material may be one of the process feed materials or another material such as nitrogen.

One or several beds of sorbent may be used. Where several beds are used, they may be combined in series or in parallel. Also, where several beds are used, the separation efficiency may be increased by use of cycling zone sorption, where the pressure and or the temperatures of the beds are alternately raised and lowered as the process stream is passed through.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLE 1

Metal robing 0.25" (6.4 mm) I.D.×4.5 in. (11.4 cm) was packed with carbon nanotubes and installed in a gas chromatograph with a flame ionization detector. The columns were heated at 200° C. in flowing helium for a minimum of 12 hours. Helium was fed as a carrier gas at 30 sccm ($5.0 \times 10^{-7}$ m$^3$/g). Samples (25 μL) of CFC-115 and HFC-125 were then injected into the carrier stream at different temperatures. The results of these experiments are shown in Table 1. These data show that in each case the compounds had different retention times, and thus may be separated using Carbon nanotubes.

TABLE 1

| | Retention Time (min.) | | |
|---|---|---|---|
| Temp. (°C.) | 115 | 125 | Separation Factor[a] |
| 50 | 4.12 | 0.89 | 4.6 |
| 75 | 1.35 | 0.42 | 3.2 |
| 100 | 0.24 | 0.25 | 1.0 |

[a]Separation Factor = 115 Retention Time/125 Retention Time

COMPARATIVE EXAMPLE

The procedure of Example 1 was used except for the sorbent which was buckminsterfullerene (buckyballs). The results of these experiments are shown in Table 2.

TABLE 2

| | Retention Time (min.) | | |
|---|---|---|---|
| Temp. (°C.) | 115 | 125 | Separation Factor[a] |
| 50 | 0.26 | 0.25 | 1.0 |

[a]Separation Factor = 115 Retention Time/125 Retention Time

What is claimed is:

1. A process for treating a starting mixture of $CHF_2CF_3$ and $CClF_2CF_3$ to provide a product wherein the mole ratio of $CHF_2CF_3$ to $CClF_2CF_3$ is increased relative to the mole ratio of $CHF_2CF_3$ to $CClF_2CF_3$ in the starting mixture, comprising:

contacting said starting mixture with sorbent of carbon nanotubes at a temperature within the range of about −20° C. to 75° C. and a pressure within the range of about 10 kPa to 3000 kPa and for a period of time sufficient to remove a substantial amount of the $CClF_2CF_3$.

2. The process of claim 1 wherein the contact is sufficient to provide a product in which the mole ratio of $CClF_2CF_3$ to $CHF_2CF_3$ is no more than 50% of the mole ratio of $CClF_2CF_3$ to $CHF_2CF_3$ in the starting mixture.

3. The process of claim 2 wherein prior to contact with the nanotubes the mole ratio of $CHF_2CF_3$ to $CClF_2CF_3$ is at least about 9:1.

4. The process of claim 3 wherein the sorbent contact is sufficient to produce $CHF_2CF_3$ of at least about 99.9 mole percent purity.

5. The process of claim 3 wherein the starting mixture consists essentially of $CClF_2CF_3$ and $CHF_2CF_3$.

6. The process of claim 5 wherein the $CClF_2CF_3$ is desorbed to provide a $CClF_2CF_3$-enriched product.

7. The process of claim 1 wherein the $CClF_2CF_3$ is desorbed to provide a $CClF_2CF_3$-enriched product.

8. A process for treating a starting mixture of $CHF_2CF_3$ and $CClF_2CF_3$ to provide a product mixture wherein the mole ratio of $CClF_2CF_3$ to $CHF_2CF_3$ is increased relative to the mole ratio of $CClF_2CF_3$ to $CHF_2CF_3$ in the starting mixture comprising:

contacting said starting mixture with a sorbent of carbon nanotubes at a temperature within the range of about −20° C. to 75° C. and a pressure within the range of about 10 kPa to 3000 kPa and for a period of time sufficient to remove a substantial amount of the $CClF_2CF_3$; and desorbing sorbed $CClF_2CF_3$ to provide a product which is enriched therewith.

\* \* \* \* \*